United States Patent
Romanet et al.

(10) Patent No.: US 6,787,294 B1
(45) Date of Patent: Sep. 7, 2004

(54) PHOTOGRAPHIC MATERIAL COMPRISING A BICYCLIC PYRAZOLOTRIAZOLE COUPLER WITH IMPROVED HUE

(75) Inventors: Robert F. Romanet, Rochester, NY (US); Susan M. Fischer, Rochester, NY (US); David G. Lincoln, Webster, NY (US); Gary M. Russo, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/602,273

(22) Filed: Jun. 24, 2003

(51) Int. Cl.[7] .......................... G03C 7/38; C07D 249/00
(52) U.S. Cl. ...................... 430/387; 430/558; 548/262.4
(58) Field of Search ................................ 430/387, 558; 548/262.4

(56) References Cited

U.S. PATENT DOCUMENTS

| | | | | |
|---|---|---|---|---|
| 4,540,654 A | * | 9/1985 | Sato et al. | .................. 430/558 |
| 4,621,046 A | * | 11/1986 | Sato et al. | ............... 548/262.4 |
| 5,248,786 A | * | 9/1993 | Tang et al. | .............. 548/262.4 |

FOREIGN PATENT DOCUMENTS

| | | |
|---|---|---|
| EP | 0 177 765 | 3/1990 |
| JP | 2001-183785 | 7/2001 |

* cited by examiner

*Primary Examiner*—Richard L. Schilling
(74) *Attorney, Agent, or Firm*—Arthur E. Kluegel

(57) ABSTRACT

Disclosed is a photographic element comprising a light sensitive silver halide emulsion layer and, having associated with that layer, a 1H-pyrazo[1,5-b]-1,2,4-triazole dye forming coupler having a fully substituted carbon atom at the 6-position, a chloro group at the 7-position, and, at the 2-position, a propionic ester moiety.

18 Claims, No Drawings

PHOTOGRAPHIC MATERIAL COMPRISING A BICYCLIC PYRAZOLOTRIAZOLE COUPLER WITH IMPROVED HUE

FIELD OF THE INVENTION

This invention relates to photographic elements, couplers and processes including novel 1H-pyrazolo[1,5-b][1,2,4]triazole-based couplers having a ring carbon bearing a propionic ester moiety.

BACKGROUND OF THE INVENTION

Color images are customarily obtained in the photographic art by reaction between an oxidation product of a silver halide developing agent and a dye-forming coupler. Pyrazolones are useful for forming magenta dye images; however, such couplers have shortcomings with respect to color reproduction in that the unwanted absorption around 430 nm causes color turbidity. Bicyclic pyrazolo couplers, particularly pyrazolotriazole couplers, represent another class of couplers for this purpose. Examples of pyrazoloazole couplers are described in, for example, U.S. Pat. Nos. 4,443,536, 4,665,015; 4,514,490; 4,621,046, 4,540,654; 4,590,153; 4,822,730 and European Patents 177,765 and 119,860. One class of pyrazolotriazole couplers includes 1H-pyrazolo[3,2-c][1,2,4]triazole couplers and another includes 1H-pyrazolo[1,5-b][1,2,4]triazole couplers, such as described in European Patent 177,765. While these couplers have a reduced level of unwanted absorption, the spectral absorption is often deeper having absorption maxima at higher wavelengths than is desired. Frequently addenda must be added to bring the hue into a usable range.

It is a problem to be solved to provide 1H-pyrazolo[1,5-b][1,2,4]triazole couplers that exhibit desirable hue characteristics.

SUMMARY OF THE INVENTION

The present invention provides a photographic element comprising a light sensitive silver halide emulsion layer and, having associated with that layer a 1H-pyrazo[1,5-b]-1,2,4-triazole dye forming coupler having a fully substituted carbon atom at the 6-position, a chloro group at the 7-position, and, at the 2-position, a propionic ester moiety.

It has been found that photographic elements containing these couplers exhibit desirable hue characteristics.

DETAILED DESCRIPTION OF THE INVENTION

Suitably, the couplers of the invention are 1H-pyrazolo[1,5-b][1,2,4]triazoles with a fully substituted carbon atom at the 6-position and a chloro group at the 7-position

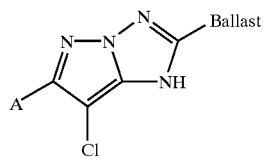

(I)

and contain a ballasting substituent in the 2-position according to formula (i)

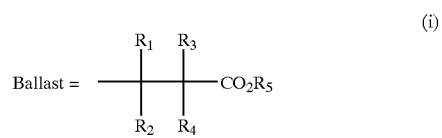

(i)

wherein A is a fully substituted carbon atom, $R_1$, $R_2$, $R_3$, and $R_4$ are independently a hydrogen or a branched or unbranched, substituted or unsubstituted, alky, aryl, or heterocyclic group and $R_5$ is a branched or unbranched, substituted or unsubstituted, alky group. Suitably, $R_1$, $R_2$, $R_3$, $R_4$, and $R_5$ may be a group known in the art that typically promotes solubility, diffusion resistance, or dye stability of the dye formed upon reaction of the coupler with the oxidized color developing agent.

A is preferably a carbon atom substituted with unsubstituted alkyl or aryl groups and more preferably a carbon atom substituted with unsubstituted alkyl or aryl groups containing eight carbons or less and most preferably being tertiary butyl. $R_1$, $R_2$, $R_3$, and $R_4$ are independently hydrogen or an alkyl or aryl groups, substituted or unsubstituted and branched or unbranched but preferably hydrogen or an unsubstituted alkyl or aryl groups and more preferably hydrogen or an unsubstituted alkyl groups and most preferably hydrogen or methyl or ethyl groups. In addition any of $R_1$, $R_2$, $R_3$, and $R_4$ may be linked to form a saturated ring. $R_5$ may be a branched or unbranched alkyl group substituted or unsubstituted but preferably a unsubstituted branched or unbranched group and more preferably unsubstituted and branched or unbranched with from 6 to 20 carbons and most preferably unsubstituted branched or unbranched with from 12 to 18 carbons.

Examples of the invention are shown below but are not limited to these:

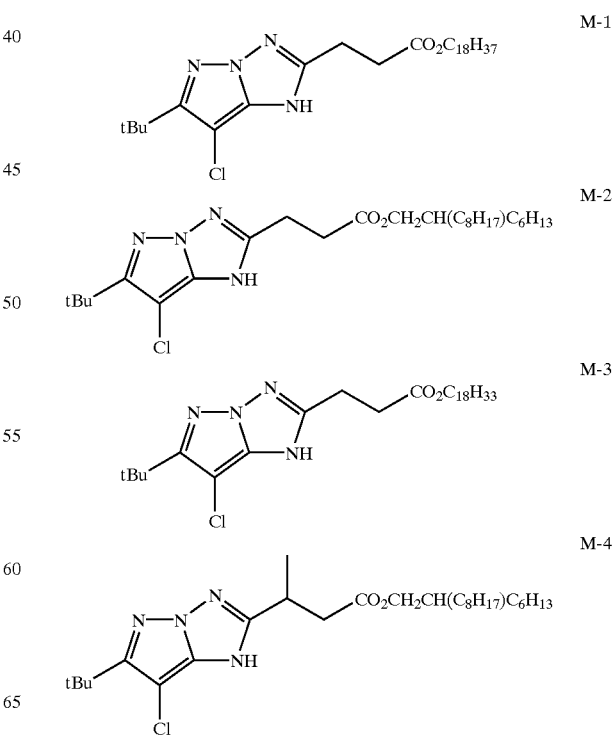

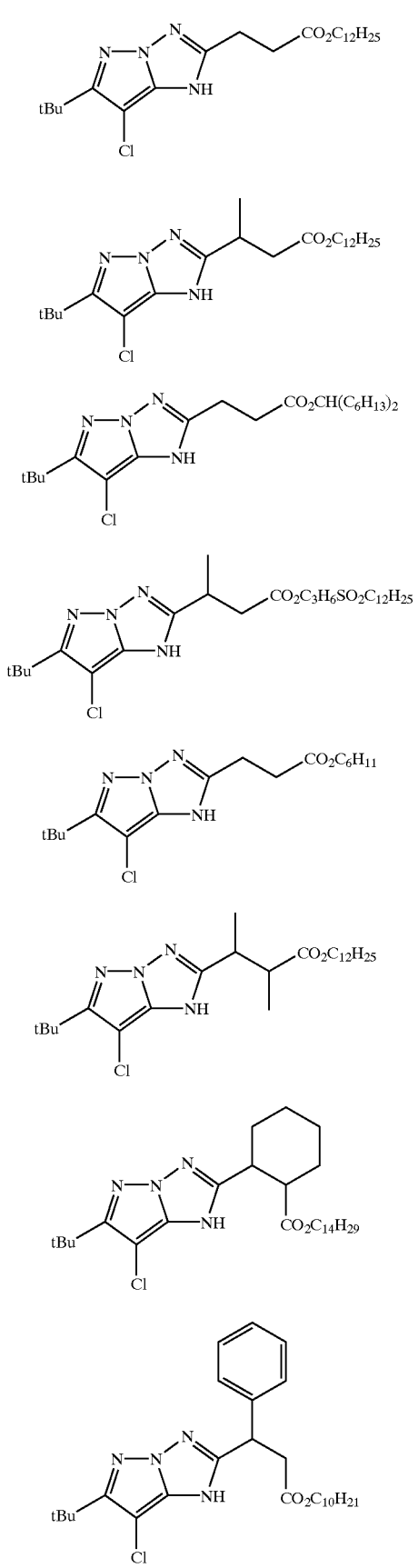
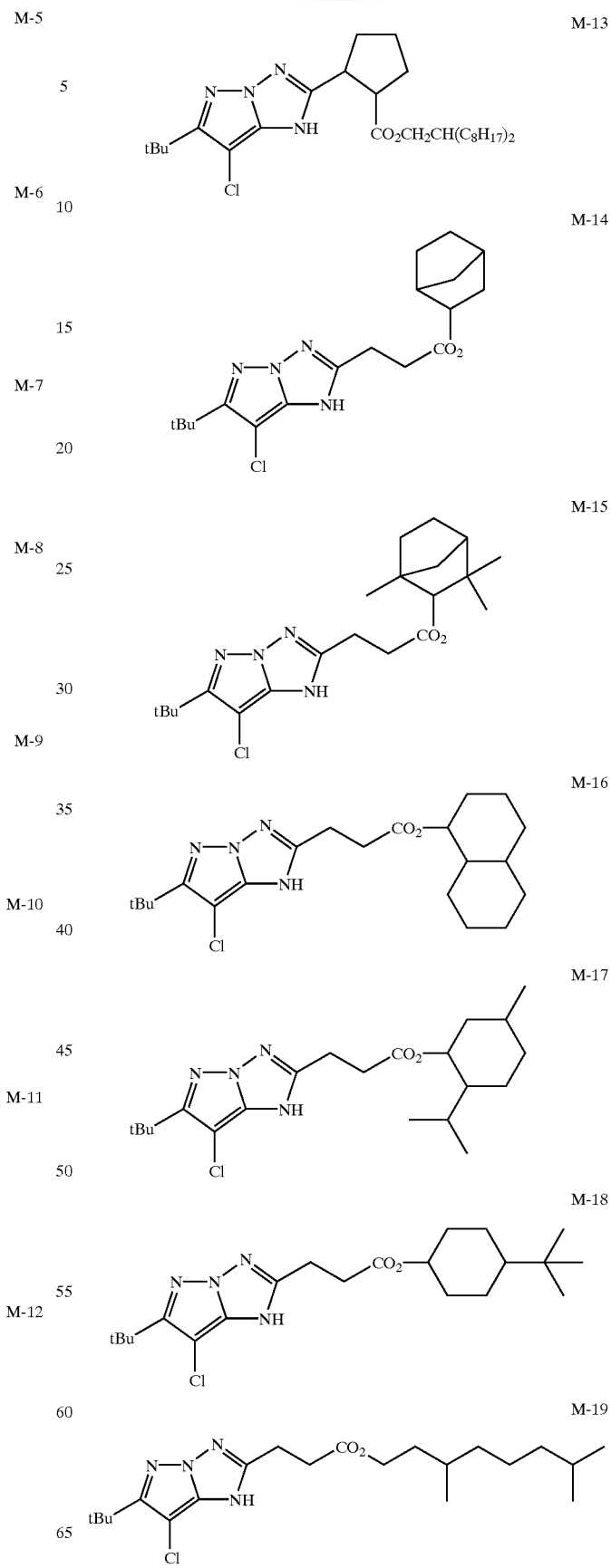

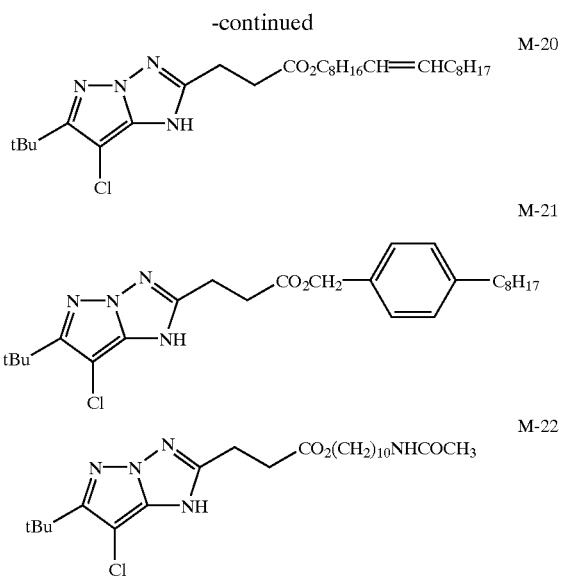

Besides good hue, embodiments of the invention exhibit good speed, dye light stability and activity.

Unless otherwise specifically stated, use of the term "substituted" or "substituent" means any group or atom other than hydrogen. Unless otherwise provided, when a group, compound or formula containing a substitutable hydrogen is referred to, it is also intended to encompass not only the unsubstituted form, but also form further substituted with any substituent group or groups as herein mentioned, so long as the substituent does not destroy properties necessary for utility. Suitably, a substituent group may be halogen or may be bonded to the remainder of the molecule by an atom of carbon, silicon, oxygen, nitrogen, phosphorous, or sulfur, The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2, 4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenoxycarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy) butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylpbenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfonyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethyiphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The materials useful in the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprising one or more red-sensitive silver halide emulsion layers, each layer having associated therewith or preferably containing a cyan dye-forming coupler, a magenta dye image-forming unit comprising one or more green-sensitive silver halide emulsion layers, each layer having associated therewith or preferably containing a magenta dye-forming coupler, and a yellow dye image-forming unit comprising one or more blue-sensitive silver halide emulsion layers, each layer having associated therewith or preferrably containing a yellow dye-forming coupler. The element can contain additional layers, such as filter layers, interlayers, overcoat layers, and subbing layers.

If desired, the photographic element can be used in conjunction with an applied magnetic layer as described in Research Disclosure, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office. When it is desired to employ the inventive materials in a small format film, Research Disclosure, June 1994, Item 36230, provides suitable embodiments.

In the following discussion of suitable materials for use in the emulsions and elements of this invention, reference will be made to Research Disclosure, September 1996, Item 38957, available as described above, which is referred to herein by the term "Research Disclosure". The Sections hereinafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 Research Disclosure, Item No. 36544 referenced above, is updated in the September 1996 Research Disclosure, Item No. 38957. Certain desirable photographic elements and processing steps, including those useful in conjunction with color reflective prints, are described in Research Disclosure, Item 37038, February 1995.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band 111, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; U.S. Pat. Nos. 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0 459 331; EPO 0 467

327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474;. 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632, 345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983,608; 4,070,191; and 4,273,861; German Applications DE 2,706,117 and DE 2,643,965; UK. Patent 1,530,272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 0.1 to 10.0 and typically 0.1 to 2.0 although dispersions using no permanent coupler solvent are sometimes employed.

The invention may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. No. 4,163, 669; U.S. Pat. No. 4,865,956; and U.S. Pat. No. 4,923,784, may be useful. Also contemplated is use in association with nucleating agents, development accelerators or their precursors (UK Patent 2,097,140; UK. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the materials useful in the invention may be blocked or coated in protected form as described, for example, in Japanese Application 61/258,249 or U.S. Pat. No. 5,019, 492.

The invention may further be used in combination with image-modifying compounds that release PUGS such as "Developer Inhibitor-Releasing" compounds (DIR's). DIR's useful in conjunction with the invention are known in the art and examples are described in U.S. Pat. Nos. 3,137, 578; 3,148,022; 3,148,062; 3,227,554; 3,384,657; 3,379, 529; 3,615,506; 3,617,291; 3,620,746; 3,701,783; 3,733, 201; 4,049,455; 4,095,984; 4,126,459; 4,149,886; 4,150, 228; 4,211,562; 4,248,962; 4,259,437; 4,362,878; 4,409, 323; 4,477,563; 4,782,012; 4,962,018; 4,500,634; 4,579, 816; 4,607,004; 4,618,571; 4,678,739; 4,746,600; 4,746, 601; 4,791,049; 4,857,447; 4,865,959; 4,880,342; 4,886, 736; 4,937,179; 4,946,767; 4,948,716; 4,952,485; 4,956, 269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in Photographic Science and Engineering, Vol. 13, p. 174 (1969). Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

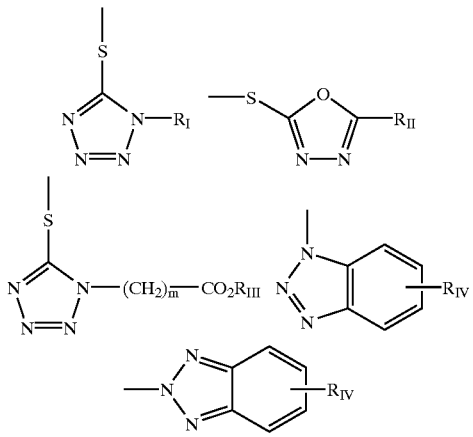

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

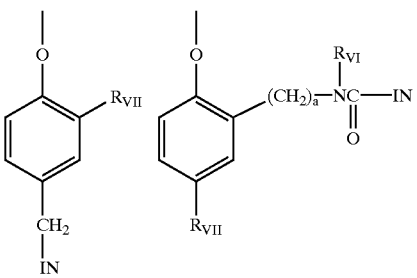

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

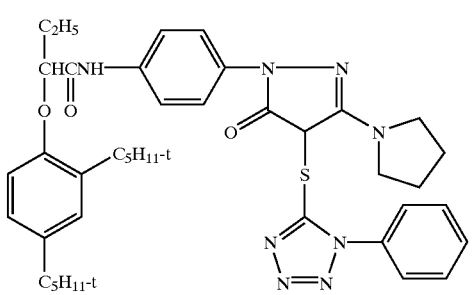

D1

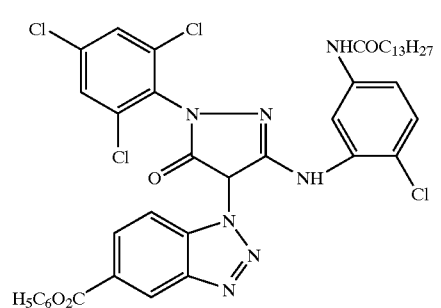

D2

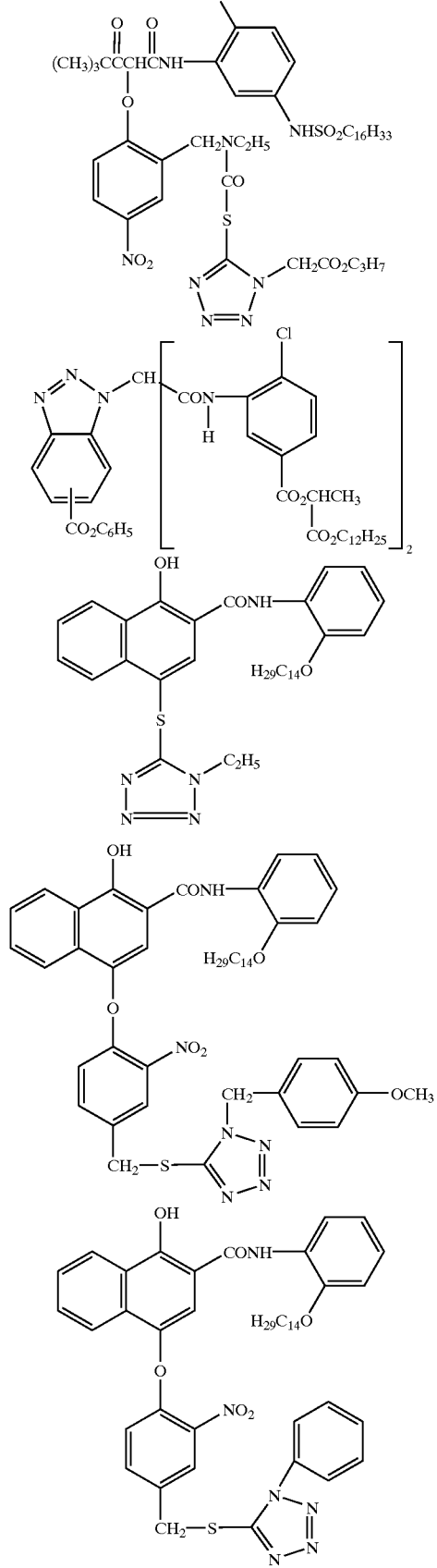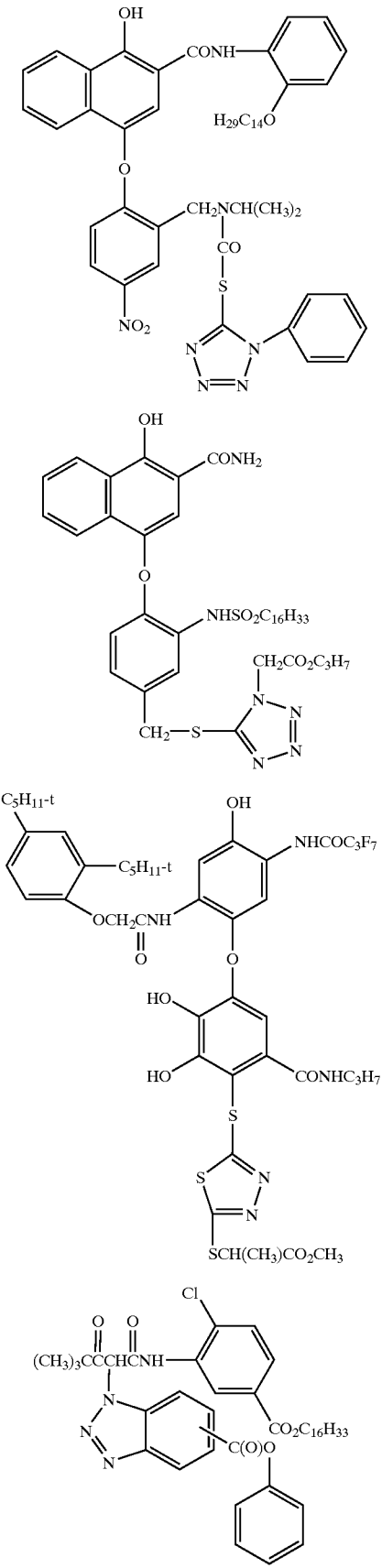

-continued

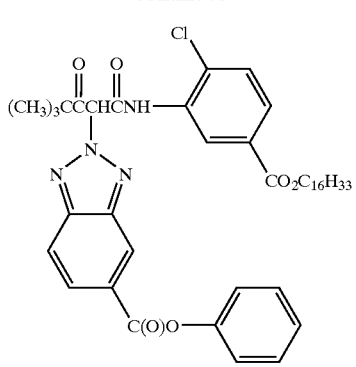

D12

It is also contemplated that the present invention may be employed to obtain reflection color prints as described in Research Disclosure, November 1979, Item 18716, available from Kenneth Mason Publications, Ltd, Dudley Annex, 12a North Street, Emsworth, Hampshire P0101 7DQ, England. Materials useful in the invention maybe coated on pH adjusted support as described in U.S. Pat. No. 4,917,994; on a support with reduced oxygen permeability (EP 553, 339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,63 1; 90-072,632; 90-072,633; 90-072, 634; 90-077,822; 90-078,229; 90-078,230; 90-079,336; 90-079,337; 90-079,338; 90-079,690; 90-079,691; 90-080, 487; 90-080,488; 90-080,489; 90-080,490; 90-080,491; 90-080,492; 90-080,494; 90-085,928; 90-086,669; 90-086, 670; 90-087,360; 90-087,361; 90-087,362; 90-087,363; 90-087,364; 90-088,097; 90-093,662; 90-093,663; 90-093, 664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by Research Disclosure, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111 } tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435, 501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061, 609, Tsaur et al U.S. Pat. Nos. 5,147,771, '772, '773, 5,171,659 and 5,252,453, Black et al 5,219,720 and 5,334, 495, Delton U.S. Pat. Nos. 5,310,644, 5,372,927 and 5,460, 934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713, 323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111 } tabular grain emulsions are illustrated by Maskasky U.S. Pat. Nos. 5,271, 858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320, 938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unf6gged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color-developing agent to reduce developable silver halide and oxidize the color-developing agent. Oxidized color developing agent in turn reacts with the coupler to yield a dye. If desired "Redox Amplification" as described in Research Disclosure XVIIIB(5) may be used.

A "color negative element" utilizes negative-working silver halide and provides a negative image upon processing. A first type of such element is a capture element, which is a color negative film that is designed for capturing an image in negative form rather than for viewing an image. A second type of such an element is a direct-view element that is designed, at least in part, for providing a positive image viewable by humans.

In the capture element, speed (the sensitivity of the element to low light conditions) is usually critical to obtaining sufficient image in such elements. Such elements are typically silver bromoiodide emulsions coated on a transparent support and are sold packaged with instructions to process in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3'15" or less and desirably 90 or even 60 seconds or less.

A direct-view photographic element is one which yields a color image that is designed for human viewing (1) by reflected light, such as a photographic paper print, (2) by transmitted light, such as a display transparency, or (3) by projection, such as a color slide or a motion picture print. These direct-view elements may be exposed and processed in a variety of ways. For example, paper prints, display transparencies, and motion picture prints are typically produced by digitally printing or by optically printing an image from a color negative onto the direct-viewing element and processing though an appropriate negative-working photographic process to give a positive color image, The element may be sold packaged with instructions for digital printing or for processing using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less. Color slides may be produced in a similar manner but are more typically produced by exposing the film directly in a camera and processing through a reversal color process or a direct positive process to give a positive color image. The foregoing images may also be produced by alternative processes such as digital printing.

Each of these types of photographic elements has its own particular requirements for dye hue, but in general they all require cyan dyes whose absorption bands are less deeply absorbing (that is, shifted away from the red end of the spectrum) than color negative films. This is because dyes in direct-view elements are selected to have the best appearance when viewed by human eyes, whereas the dyes in image capture materials are designed to best match the needs of the printing process.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal elements are typically sold packaged with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

The photographic element of the invention can be incorporated into exposure structures intended for repeated use or exposure structures intended for limited use, variously referred to by names such as "single use cameras", "lens withfilm", or "photosensitive material package units".

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonainidoethyl)aniline sesquisulfate hydrate, 4-amino-3-methyl-N-ethyl-N-(2-hydroxyethyl)aniline sulfate, 4-amino-3-(2-methanesulfonamidoethyl)-N,N-diethylaniline hydrochloride, and 4-amino-N-ethyl-N-(2-methoxyethyl)-m-toluidine di-ptoluene sulfonic acid.

Development is usually followed by the conventional steps of bleaching, fixing, or bleach-fixing, to remove silver or silver halide, washing, and drying.

The synthesis of compounds of the invention are carried out by standard methods. The synthesis of M-1 is shown below for illustrative purposes.

EXAMPLES

SYNTHESIS OF M-1

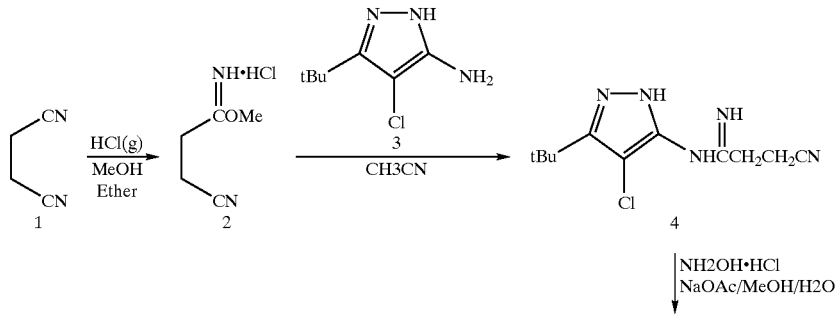

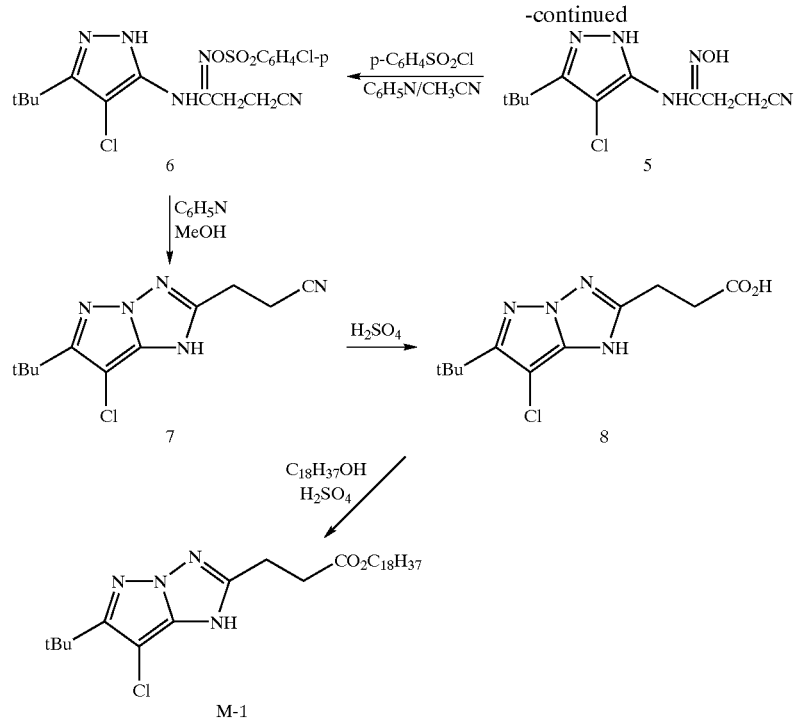

Synthesis of Imino Ether 1:

42.9 g malonitrile 1 was dissolved in 400 ml ethyl ether, 100 ml methylene chloride, and 21.4 ml methanol and cooled to 10° C. in an ice bath. Hydrogen chloride gas was bubbled through for 30 minutes at such a rate to keep the temperature under 20° C. After 15 minutes a white solid started precipitating. After storing in the refrigerator over the weekend the while solid was filter off and washed with ethyl ether and dried under nitrogen to yield 78.4 g of product 1.

Formation of Amidine 4:

15 m of aminopyrazole 3 and 12.9 g of imino ether 2 were stirred together in 150 ml acetonitrile at ice bath temperature. The ice let melt and the reaction stirred ambient temperatures overnight. 24 g pink solid was filtered off and used in the next step.

Formation of Oxime 5:

24 g 4 and 8.7 g hydroxylamine hydrochloride stirred in 200 ml methanol and 12 g sodium acetate in 24 ml water added over 5 minutes. The mixture refluxed one hour, most of the solvent evaporated off and the residue dissolved in ethylacetate and washed 3 times with brine, dried over $MgSO_4$ and evaporated. The residue crystallized from eihylacetate/heptane (70/30) to yield 6 g white solid.

Formation of 6:

6 g 5 dissolved in 50 ml THF, cooled to ice bath temperature and 4.6 g p-chlorobenrzenesulfonyl chloride added followed by 1.8 ml pyridine. After two minutes the ice bath was removed and the mixture stirred over the weekend. The reaction dissolved in ethyl acetate and washed with dilute HCl followed by water and the organic layer dried over $MgSO_4$ and evaporated to an off white solid.

Formation of 7:

7.5 g of 6, 1.4 ml pyridine, and 80 ml of methanol were refluxed 5 hours. The reaction poured into dilute HCl, ethyl acetate added and the organic layer washed 3 times with water, dried over $MgSO_4$ and evaporated to a brown solid. Trituration with isopropyl ether gave 2.9 gram pure product.

Formation of 8:

3.7 g 7 refluxed with 120ml water and 120 ml sulfuric acid for one hour. The reaction diluted with water and the product filtered off and dried.

Formation of M-1:

0.5 g 8 was stirred with 1.0 gm of octadecanol containing 4 drops of sulfuric acid for 3 days. 4 more drops acid added and after 3 more days water and ethyl acetate was added and the organic layer washed 3 times with water and dried over $MgSO_4$ and evaporated. The residue chromatographed on $SiO_2$ with 30% ethyl acetate in heptane and crystallized from acetonitrile to give 0.35 g M-1 as a white solid, .mp 62° C.

Photographic Example

The invention was evaluated in a coating containing a single coupler and consisting of 3 layers. Evaluations were made based on samples of these coatings. The invention will be described in more detail using coating experiment 1, however the invention is not limited to this experiment. Dispersions of example couplers, were emulsified by methods well known to the art, and were coated on the face side of a doubly extruded polyethylene coated color paper support using conventional coating techniques. The gelatin layers were hardened with bis (vinylsulfonyl methyl) ether at 1.8% of the total gelatin.

Experiment 1 was made by coating photosensitive emulsions on a resin-coated photographic support with 3.22 g/m² of gelatin as base.

| Experiment 1 | |
|---|---|
| 1st layer - Magenta Coupler Layer | |
| Gelatin | 1.44 g/m² |
| Compound M-1 | 0.04 mmol |
| High Boiling Organic Solvent/coupler ratio | 4 |
| Stabilizer 1/coupler molar ratio | 0.367 |
| Stabilizer 2/coupler molar ratio | 1.698 |

-continued

Experiment 1

| | |
|---|---|
| Emulsion for Magenta Emulsion (Fine Grain silver iodide emulsion, average equivalent grain size 0.64 μm) | 0.107 g/m² |
| 2nd layer UV Absorbing Layer | |
| Gelatin | 1.40 g/m² |
| UV Absorbent | 0.613 g/m² |
| 3rd Layer Protective Layer | |
| Gelatin | 1.40 g/m² |
| Gel Hardening Compound BVSME | 1.8% of total gel |

High Boiling Organic Solvent

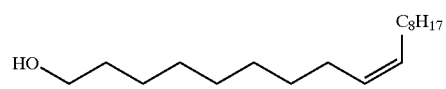

Stabilizer 1

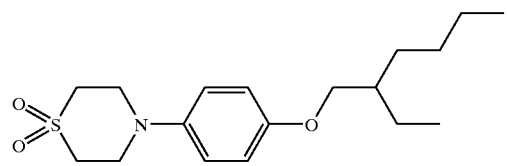

Stabilizer 2

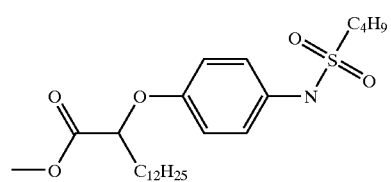

UV Absorbent

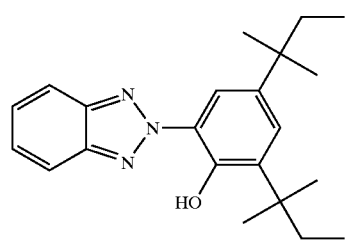

Once the coated paper samples, described above had been prepared, they were given a prelimiynar evaluation as follows:

The respective paper sampless Were exposed in a Kodak Model 1B sensitometer with a color temperature of 3000° K and filtered with a Kodak Wratten™ 2C plus a Kodak Wratten™ 29 filter and a Hoya HA-50. Exposure time was adjusted to 0.1 seconds. The exposures were performed by contacting the paper samples with a neutral density step exposure tablet having an exposure range of 0 to 3 log-E.

The paper samples described above were processed in the Kodak Ektacolor RA-4 Color Development™ process. The color developer and bleach-fix formulations are described below in Tables 1 and 2. The chemical development process cycle is described in Table 3.

TABLE 1

Kodak Ektacolor ™ RA-4 Color Developer

| Chemical | Grams/Liter |
|---|---|
| Triethanol amine | 12.41 |
| Phorwite REU ™ | 2.30 |
| Lithium polystyrene sulfonate (30%) | 0.30 |
| N,N-diethylhydroxylamine (85%) | 5.40 |
| Lithium sulfate | 2.70 |
| Kodak color developer CD-3 (with 4-amino-3-methyl-N-ethyl-N-(2-methanesulfonamidoethyl)aniline sesquisulfate hydrate developer) | 5.00 |
| DEQUEST 2010 ™ (1-Hydroxyethyl-1,1-diphosphonic acid (60%) | 1.16 |
| Potassium carbonate | 21.16 |
| Potassium bicarbonate | 2.79 |
| Potassium chloride | 1.60 |
| Potassium bromide | 0.007 |
| Water | to make 1 liter | pH @ 26.7° C. is 10.04 +/− 0.05

TABLE 2

Kodak Ektacolor ™ RA-4 Bleach-Fix

| Chemical | Grams/Liter |
|---|---|
| Ammonium thiosulfate (56.5%) | 127.40 |
| Sodium metabisulfite | 10.00 |
| Glacial acetic acid | 10.20 |
| Ammonium ferric EDTA (44%) | 110.40 |
| Water | to make 1 liter | pH @ 26.7° C. is 5.5 +/− 0.10

TABLE 3

Kodak Ektacolor ™ RA-4 Color Paper Process

| Process Step | Time (seconds) |
|---|---|
| Color Development | 45 |
| Bleach-fix | 45 |
| Wash | 90 |
| Dry | |

Processing the exposed paper samples is performed with the developer and bleach-fix temperatures adjusted to 35° C. Washing is performed with tap water at 32.2° C. The samples were evaluated for hue as shown in Table 4 below.

TABLE 4

Results

| COUPLER | STRUCTURE of 2-Substituent | Δλmax (C-3 - Sample)* in nm |
|---|---|---|
| M-1 | ~~CO₂C₁₈H₃₇ | 3.5 |
| M-2 | ~~CO₂CH₂CH(C₆H₁₃)C₈H₁₇ | 4.1 |
| M-3 | CH₃-CH-CO₂C₁₂H₂₅ | 5.9 |
| M-4 | ~~CO₂C₁₂H₂₅ | 5.6 |
| C-1 | ~~CONHC₁₈H₃₇ | −1.7 |
| C-2 | ~~OCONHC₁₈H₃₇ | −0.1 |
| C-3 | ⌬—NHCOCH₂CH₂CO₂C₁₄H₂₉ | 0** |

*Hypso shift from C-3
**Average value for C-3 comparison = 552.5 nm

As can be seen from the table, couplers of this invention (M-1, M-2, M-3, M-4) have hues hypsochromic to the check couplers (C-1, C-2, C-3) and are in the desirable 546 to 549 range. The check couplers exhibit maximum absorptions above 549 nm.

The invention has been described in detail with particular reference to certain preferred embodiments thereof, but it will be understood that variations and modifications can be effected within the scope of the invention. The entire contents of the patents and other publications referred to in this specification are incorporated herein by reference.

What is claimed is:

1. A photographic element comprising a light sensitive silver halide emulsion layer and, having associated with that layer, a 1H-pyrazo[1,5-b]-1,2,4-triazole dye forming coupler having a fully substituted carbon atom at the 6-position, a chloro group at the 7-position, and, at the 2-position, a propionic ester moiety.

2. The element of claim 1 wherein the propionic ester moiety is substituted at the 1- or 2-position.

3. The element of claim 1 wherein the second ring carbon position bears a ballast containing at least 6 aliphatic carbon atoms.

4. The element of claim 1 wherein the propionic ester is an alkyl ester.

5. The element of claim 1 wherein the 6-substituent is a t-butyl group.

6. The element of claim 1 wherein the coupler is selected so that the wavelength of maximum absorption of the dye formed by the coupler, using 4-amino-3-methyl-N-ethyl-N-(2-methanesulfonamidoethyl)aniline sesquisulfate hydrate as developer, is in the range of 546–549 nm.

7. The element of claim 1 wherein the coupler is represented by Formula (I):

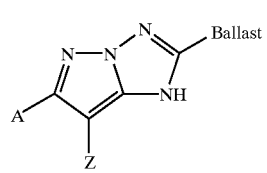

(I)

wherein A is a fully substituted carbon atom, Z is Cl and Ballast is the group (i):

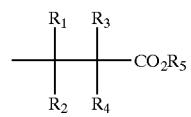

(i)

wherein $R_1$ through $R_4$ are independently H or substituents, two of which may be linked to form a saturated ring, and $R_5$ is an alkyl group.

8. The element of claim 7 wherein $R_1$ through $R_4$ are independently H, alkyl, or aryl groups.

9. The element of claim 7 wherein $R_1$ through $R_4$ are independently H or alkyl groups.

10. The element of claim 7 wherein $R_1$ through $R_4$ are independently H or methyl or ethyl groups.

11. The element of claim 7 wherein A is fully substituted with alkyl or aryl groups containing up to 8 carbon atoms.

12. The element of claim 7 wherein A is a t-butyl group.

13. The element of claim 7 wherein $R_5$ is an unsubstituted alkyl group.

14. The element of claim 13 wherein $R_5$ is an alkyl group of 6 to 20 carbon atoms.

15. The element of claim 13 wherein $R_5$ is an alkyl group of 12 to 18 carbon atoms.

16. A process for forming an image comprising imagewise exposing the element of claim 1 to light and the contacting the exposed element to a developer.

17. The process of claim 16 wherein the developer is a para phenylene diamine.

18. A coupler represented by Formula (I):

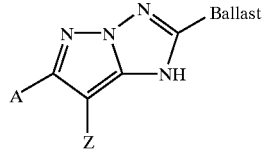
(I)

wherein A is a fully substituted carbon atom, Z is Cl and Ballast is the group (i)

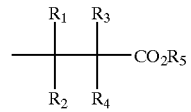
(i)

wherein $R_1$ through $R_4$ are independently H or substituents, two of which may be linked to form a saturated ring, and $R_5$ is an alkyl group containing at least 6 aliphatic carbon atoms.

* * * * *